United States Patent
Ring et al.

(10) Patent No.: US 6,825,182 B2
(45) Date of Patent: Nov. 30, 2004

(54) 17α-FLUOROALKYL-11β-BENZALDOXIME STEROIDS, PROCESS FOR THEIR PRODUCTION, PHARMACEUTICAL PREPARATIONS THAT CONTAIN THESE STEROIDS AS WELL AS THEIR USE FOR THE PRODUCTION OF PHARMACEUTICAL AGENTS

(75) Inventors: Sven Ring, Jena (DE); Gerd Schubert, Jena (DE); Ingo Tornus, Hennigsdorf (DE); Guenter Kaufmann, Jena (DE); Walter Elger, Berlin (DE); Birgitt Schneider, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/429,247

(22) Filed: May 5, 2003

(65) Prior Publication Data
US 2004/0092492 A1 May 13, 2004

Related U.S. Application Data
(60) Provisional application No. 60/449,401, filed on Feb. 25, 2003.

(30) Foreign Application Priority Data
May 3, 2002 (DE) .......................... 102 21 034

(51) Int. Cl.$^7$ ............................. A61K 31/56; C07J 1/00
(52) U.S. Cl. ...................................... 514/179; 552/648
(58) Field of Search ......................... 514/179; 552/648

(56) References Cited
U.S. PATENT DOCUMENTS

| | | | |
|---|---|---|---|
| 5,043,332 A | 8/1991 | Teutsch et al. | |
| 5,576,310 A | 11/1996 | Schubert et al. | |
| 5,693,628 A | 12/1997 | Schubert et al. | |
| 6,316,432 B1 | 11/2001 | Schwede et al. | |
| 6,365,582 B1 | 4/2002 | Schubert et al. | |

FOREIGN PATENT DOCUMENTS

| | | |
|---|---|---|
| DE | 43 32 284 | 3/1995 |
| DE | 43 32 283 | 4/1995 |
| DE | 197 06 061 | 8/1998 |
| DE | 198 09 845 | 9/1999 |
| EP | 0 057 115 | 8/1982 |
| EP | 0 909 764 | 4/1999 |

Primary Examiner—Barbara P. Badio
(74) Attorney, Agent, or Firm—Millen, White, Zelano & Branigan, P.C.

(57) ABSTRACT

Compounds of general formula I as well as their pharmaceutically compatible salts are described, in which $R_1$ stands for hydrogen, $C_1$- to $C_6$-alkyl, $COR_4$, $COOR_4$, $COSR_4$ or $CONHR_5$, in which $R_4$ is $C_1$- to $C_6$-alkyl or unsubstituted or substituted aryl and in which $R_5$ is hydrogen, $C_1$- to $C_6$-alkyl or unsubstituted or substituted aryl, in which $R_2$ also stands for hydrogen, $C_1$- to $C_6$-alkyl or $C_1$- to $C_6$-acyl, and $R_3$ stands for a $C_nF_{2n+1}$ group, in which n=1, 2 or 3, or a $CH_2O(CH_2)_mC_nF_{2n+1}$ group, in which m=0 or 1 and n=1, 2 or 3. In addition, a process for the production of the compounds with general formula I is indicated. The compounds can be used for the production of pharmaceutical agents.

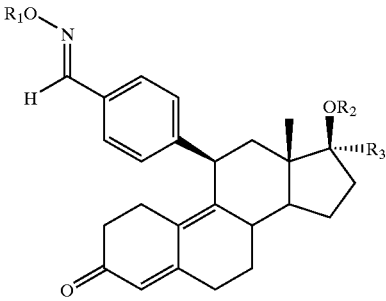

I

10 Claims, No Drawings

17α-FLUOROALKYL-11β-BENZALDOXIME STEROIDS, PROCESS FOR THEIR PRODUCTION, PHARMACEUTICAL PREPARATIONS THAT CONTAIN THESE STEROIDS AS WELL AS THEIR USE FOR THE PRODUCTION OF PHARMACEUTICAL AGENTS

This applicant claims the benefit of U.S. Provisional Application No. 60/449,401 filed Feb. 25, 2003.

DESCRIPTION

This invention relates to new 17α-fluoroalkyl-11β-benzaldoxime steroids, a process for their production, pharmaceutical preparations that contain these active ingredients as well as their use for the production of pharmaceutical agents, especially for postmenopausal substitution therapy of gynecological diseases, such as hysteromyomas or dysmenorrhoic symptoms.

Antigestagenically active steroids are already known from EP 0 057 115 A2. In this connection, this can be 3-oxo-estra-4,9-dienes substituted in 11-position.

11β-Benzaldoximes of the steroid series that have special antigestagenic properties are known from DE 43 32 283 A1, DE 43 32 284 A1, and DE 198 09 845 A1 (WO 9945023 A1).

Described in DE 43 32 283 A1 and DE 43 32 284 A1 are 11β-benzaldoxime-3-oxo-estra-4,9-diene derivatives, which can be substituted according to DE 43 32 283 A1 in 17β-position with hydroxy, alkoxy, acyloxy or aryloxy and in 17α-position with ω-fluoroalkyl.

In DE 198 09 845 A1, substituted 11β-benzaldoxime-3-oxo-estra-4,9-dienes are described. In this case, these are S-substituted carboxylic acid thiol esters of these compounds. The compounds can also be substituted in 17β-position with hydroxy, alkoxy, acyloxy or aryloxy and in 17α-position with ω-fluoroalkyl.

By contrast, steroids with 17α-fluoroalkyl chains are disclosed in DE 197 06 061 A1. These compounds, especially ZK 230211 (11β-(4-acetylphenyl)-17β-hydroxy-17α-(1,1,2,2,2-pentafluoroethyl)-estra-4,9-dien-3-one): U. Fuhrmann; H. Hess-Stumpp, A. Cleve, G. Neef, W. Schwede, J. Hoffmann, K.-H. Fritzemeier and K. Chwalisz: *J. Med. Chem.*, 2000, 43, 5010–5016), show an almost purely antagonistic activity, high receptor selectivity and, i.a., antiproliferative activity in the tumor models.

The object on which this invention is based consists in finding active ingredients with antigestagenic action that have significantly reduced antiglucocorticoidal action compared to the known compounds and that are suitable for postmenopausal substitution therapy or for treatment of gynecological diseases, such as hysteromyomas or dysmenorrhoic symptoms.

Another object on which this invention is based consists in finding a process for the production of active ingredients.

In addition, an object exists in finding pharmaceutical preparations that contain the active ingredients.

The compounds according to the invention have general formula I:

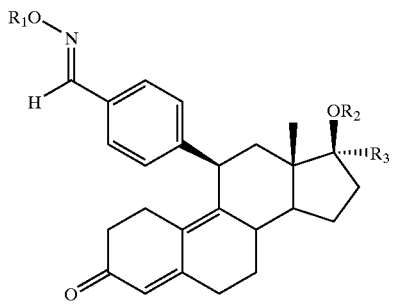

in which $R_1$ stands for hydrogen, $C_1$- to $C_6$-alkyl, $COR_4$, $COOR_4$, $COSR_4$ or $CONHR_5$, in which $R_4$ is $C_1$- to $C_6$-alkyl or unsubstituted or substituted aryl, and in which $R_5$ is hydrogen, $C_1$- to $C_6$-alkyl or unsubstituted or substituted aryl, $R_2$ stands for hydrogen, $C_1$- to $C_6$-alkyl or $C_1$- to $C_6$-acyl, and $R_3$ stands for a $C_nF_{2n+1}$ group, in which n=1, 2 or 3, or for a $CH_2O(CH_2)_mC_nF_{2n+1}$ group, in which m=0 or 1 and n=1, 2 or 3.

In all other positions of the steroid skeleton as well as on the phenylene radical in 11β-position, any other substituents, especially alkyl and aryl groups, can be bonded instead of hydrogen. In addition, this invention relates to pharmaceutically compatible salts of these compounds. Such acid addition salts can be salts of inorganic and organic acids, for example salts of hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Other usable acids are described in, for example: *Fortschritte der Arzneimittelforschung* [*Progress in Pharmaceutical Agent Research*], Vol. 10, pages 224–225, Birkhäuser Verlag, Basel and Stuttgart, 1966 as well as in: *Journal of Pharmaceutical Sciences*, Vol. 66, pages 1–5 (1977).

Radicals $R_1$ that are mentioned in this invention are especially a hydrogen atom or a methyl group or acyl groups, such as, for example, formyl, acetyl, propionyl and benzoyl radicals, or carboxylic acid ester groups, for example methoxycarbonyl radicals or ethoxycarbonyl radicals, or carboxylic acid thiol ester groups, such as methylthiocarbonyl radicals or ethylthiocarbonyl radicals, or urethane groups, such as ethylaminocarbonyl radicals or unsubstituted or substituted phenylaminocarbonyl radicals. The substituted phenylaminocarbonyl radical is preferably substituted with a $C_1$- to $C_6$-perfluoroalkyl radical.

$R_2$ preferably stands for a hydrogen atom, a methyl group or an acetyl group.

$R_3$ stands in particular for a perfluoroalkyl with n=1, 2 or 3. $R_3$ can thus stand for 1,1,1-trifluoromethyl, 1,1,2,2,2-pentafluoroethyl or 1,1,2,2,3,3,3-heptafluoropropyl. In addition, $R_3$ can stand for 1,1,1-trifluoroethyloxymethyl, if $R_3$ is provided by general formula $CH_2O(CH_2)_mC_nF_{2n+1}$, and in this case, m=1 and n=1.

The compounds according to the invention are especially the following 17α-fluoroalkyl-11β-benzaldoxime steroids:

1) 4-[17β-Hydroxy-17α-(1,1,1-trifluoromethyl)-3-oxoestra-4,9-dien-11β-yl]benzaldehyde-1(E)-oxime
2) 4-[17β-Hydroxy-17α-(1,1,1-trifluoromethyl)-3-oxoestra-4,9-dien-11β-yl]benzaldehyde-1(Z)-oxime 3) 4-[17β-Hydroxy-17α-(1,1,1-trifluoromethyl)-3-oxoestra-4,9-dien-11β-yl]benzaldehyde-1(E)-[O-(ethylamino)carbonyl]oxime
4) 4-[17β-Hydroxy-17α-(1,1,2,2,2-pentafluoroethyl)-3-oxoestra-4,9-dien-11β-yl]benzaldehyde-1(E)-oxime
5) 4-[17β-Hydroxy-17α-(1,1,2,2,2-pentafluoroethyl)-3-oxoestra-4,9-dien-11β-yl]benzaldehyde-1(E)-O-acetyloxime
6) 4-[17β-Hydroxy-17α-(1,1,2,2,2-pentafluoroethyl)-3-oxoestra-4,9-dien-11β-yl]benzaldehyde-1(E)-[O-(ethylamino)carbonyl]oxime
7) 4-[17β-Hydroxy-17α-(1,1,2,2,2-pentafluoroethyl)-3-oxoestra-4,9-dien-11β-yl]benzaldehyde-1(E)-[O-(ethylthio)carbonyl]oxime
8) 4-[17β-Hydroxy-17α-(1,1,2,2,2-pentafluoroethyl)-3-oxoestra-4,9-dien-11β-yl]benzaldehyde-1(E)-[O-(ethoxy)carbonyl]oxime
9) 4-[17β-Hydroxy-17α-(1,1,2,2,2-pentafluoroethyl)-3-oxoestra-4,9-dien-11β-yl]benzaldehyde-1(E)-[O-(methoxy)carbonyl]oxime
10) 4-[17β-Hydroxy-17α-(1,1,2,2,3,3,3-heptafluoropropyl)-3-oxoestra-4,9-dien-11β-yl]benzaldehyde-1(E)-oxime
11) 4-[17β-Methoxy-17α-(1,1,1-trifluoromethyl)-3-oxoestra-4,9-dien-11β-yl]benzaldehyde-1(E)-oxime
12) 4-[17β-Methoxy-17α-(1,1,1-trifluoromethyl)-3-oxoestra-4,9-dien-11β-yl]benzaldehyde-1(E)-[O-(ethylamino)carbonyl]oxime
13) 4-[17β-Methoxy-17α-(1,1,2,2,2-pentafluoroethyl)-3-oxoestra-4,9-dien-11β-yl]benzaldehyde-1(E)-oxime
14) 4-[17β-Methoxy-17α-(1,1,2,2,2-pentafluoroethyl)-3-oxoestra-4,9-dien-11β-yl]benzaldehyde-1(E)-O-acetyloxime
15) 4-[17β-Methoxy-17α-(1,1,2,2,2-pentafluoroethyl)-3-oxoestra-4,9-dien-11β-yl]benzaldehyde-1(E)-[O-(ethylamino)carbonyl]oxime
16) 4-[17β-Methoxy-17α-(1,1,2,2,2-pentafluoroethyl)-3-oxoestra-4,9-dien-11β-yl]benzaldehyde-1(E)-{O-[(4'-trifluoromethyloxy)phenylamino]carbonyl}oxime
17) 4-[17β-Methoxy-17α-(1,1,2,2,2-pentafluoroethyl)-3-oxoestra-4,9-dien-11β-yl]benzaldehyde-1(E)-[O-(ethoxy)carbonyl]oxime
18) 4-[17β-Methoxy-17α-(1,1,2,2,2-pentafluoroethyl)-3-oxoestra-4,9-dien-11β-yl]benzaldehyde-1(E)-[O-(methoxy)carbonyl]oxime
19) 4-[17β-Methoxy-17α-(1,1,2,2,2-pentafluoroethyl)-3-oxoestra-4,9-dien-11β-yl]benzaldehyde-1(E)-[O-(ethylthio)carbonyl]oxime
20) 4-[17β-Acetoxy-17α-(1,1,2,2,2-pentafluoroethyl)-3-oxoestra-4,9-dien-11β-yl]benzaldehyde-1(E)-[O-(ethylamino)carbonyl]oxime
21) 4-[17β-Acetoxy-17α-(1,1,2,2,2-pentafluoroethyl)-3-oxoestra-4,9-dien-11β-yl]benzaldehyde-1(E)-oxime
22) 4-[17β-Hydroxy-17α-[(1,1,1-trifluoroethyloxy)methyl]-3-oxoestra-4,9-dien-11β-yl]benzaldehyde-1(E)-oxime In the prior art documents, the 17α-fluoroalkyl-11β-benzaldoxime steroids and ester, thiol ester or urethane derivatives thereof are not disclosed. The compounds according to the invention are therefore new and not previously known from the literature. The biological profile of action of the above-mentioned compounds is not described. It is not possible to cover all potential applications with an "antigestagen" (W. Elger, K. Chwalisz, *Reproduktions-medizin* [*Reproduction Medicine*], 1999, 15, 318–335; I. M. Spitz, H. J. Bennink: *Steroids*, 2000, 65 837–838). The compounds according to the invention are suitable for postmenopausal substitution therapy, also in combination with an estrogen, or can be used for treatment of gynecological diseases, such as hysteromyomas or dysmenorrhoic symptoms.

This invention also relates to a production process for the 17α-fluoroalkyl-11β-benzaldoxime steroids according to the invention.

The 17α-fluoroalkyl groups can be introduced into the steroid skeleton by a 17-ketone being used as a starting material according to methods that are known in the art. Ruppert had described the production of trifluoromethyltrimethylsilane (*Tetrahedron Letters*, 1984, 25, 2195), which is highly suitable for the introduction of the trifluoromethyl group from aldehydes and ketones in the presence of tetrabutylammonium fluoride. (R. Krishnamurti, D. R. Bellew, G. K. S. Prakash, *J. Org. Chem.*, 1991, 56, 984 and Lamberth, *J. Prakt. Chem.*, 1996, 338, 586–587, Ruppert's Reagent).

To introduce the homologous fluoroalkyl groups into the steroid skeleton, 17-ketones can be used as a starting material. To this end, processes were described in which fluoroalkyl compounds with the general formula halogen-$C_nF_{2n+1}$ are reacted in situ with metal to form organometallic compounds of the alkali or alkaline-earth series with the general formula metal-$C_nF_{2n+1}$. The latter can then be reacted with the 17-ketones to form 17 α-fluoroalkyl-17β-hydroxy compounds. (DE 197 06 061 A1). The 17α-fluoroalkoxymethyl grouping can preferably be introduced by a ring opening reaction from a corresponding 17(20)-spiroepoxide [Ponsold, Hübner, Schnabel, Strecke, *Arzneimittel-Forschung* [*Pharmaceutical Agent Research*] (*Drug Res.*), 24 (1974) 896–900].

The process for the production of the starting materials with general formula II:

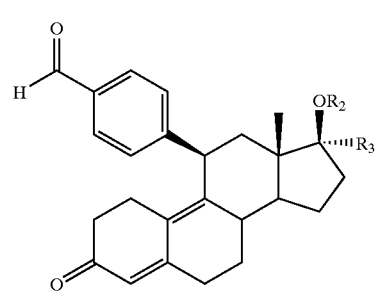

II which are required for the production of the compounds according to the invention with general formula I, is described in EP 0 411 733 A2 and DE 43 32 283 A1:

For the production of the compounds with general formula II, for example, a compound that is indicated with general formula III below can be used, whereby $R^{3'}$, $R^{4'}$, $R^{6'}$, $R^{7'}$ and $R^{8'}$ have the meaning of corresponding radicals $R^{3'}$, $R^{4'}$, $R^6$, $R^7$ or $R^8$ that are indicated in EP 0 411 733 A2 in formula II:

III

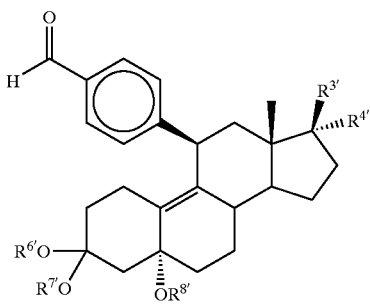

and in this connection, the latter are converted under acid treatment in a water-miscible solvent, optionally while being heated, in a compound in which the radicals are reacted in 3-position to form a 3-oxo group, and a $\Delta^{4,5}$-double bond in the steroid skeleton is formed by release of the hydroxy group in 5α-position. In this connection, more detailed information is contained in EP 0 411 733 A2, which is incorporated herewith in this application as a disclosure. The processes that are used for the production of compounds with general formula III, which depend on the ultimately desired substituents of the compounds according to the invention, are also indicated in more detail in EP 0 411 733 A2. Therefore, the disclosure that is related thereto in this document is also incorporated in this application. The corresponding data in DE 43 32 283 A1 for the production of compounds with general formula II are also incorporated as disclosures in this application.

To form the benzaldoxime group and thus to produce the compounds of general formula I according to the invention, it is proposed in a way according to the invention to react the compound with general formula II that is obtained by introducing the fluorinated alkyl group in 17β-position with a salt of a hydroxylamine in a basic solvent, such that a 17α-fluoroalkyl-11β-benzaldoxime steroid is produced, in which $R_1$ is hydrogen, and then optionally to esterify this compound, to etherify it or to convert it into a corresponding carbamate, carboxylic acid derivative or thiocarboxylic acid derivative. The additional radicals $R_2$ and $R_3$ in this general formula have the meanings that are further indicated above. The salt of the hydroxylamine in this case is preferably a hydrochloride or hydrosulfate. The basic solvent is preferably pyridine.

For the production of the compounds according to the invention, the compound with general formula II can be reacted in an alternative embodiment of the invention also with a compound with general formula $NH_2$—O—$R_1$, in which $R_1$ has the previously-mentioned meaning. Also, in this connection, reference is made to the corresponding description in DE 43 32 283 A1, which is incorporated herewith in the disclosure of this application.

The methods for the in-vitro tests and the in-vivo tests with the compounds according to the invention can be found in EP 0 411 733 A2 and DE 43 32 283 A1:

The 17α-fluoroalkyl-11β-benzaldoxime steroids according to the invention are bonded to the progesterone receptor (cf. Table 1) and in comparison to RU 486 (11β-(4-dimethylaminophenyl)-17β-hydroxy-17α-propinyl-estra-4, 9-dien-3-one) generally have a considerably reduced anti-glucocorticoidal action, detected by the reduced glucocorticoid receptor bond in vitro (cf. Table 1).

TABLE 1

Receptor Bond of
17α-Fluoroalkyl-11β-benzaldoxime Steroids

| Compound according to Example | Relative Molar Binding-affinity RBA (%) to the Progesterone Receptor Progesterone = 100% | Relative Molar Binding-affinity RBA (%) to the Glucocorticoid Receptor Dexamethasone = 100% |
|---|---|---|
| 1 | 272 | 163 |
| 2 | 123 | 113 |
| 3 | 98 | 187 |
| 4 | 23 | 10 |
| 5 | 0.5 | 10 |
| 6 | 230 | 84 |
| For comparison: | | |
| RU 486 (Mifepristone)* | 506 | 685 |
| Onapristone | 22 | 39 |

*RU 486: 11β-(4-Dimethylaminophenyl)-17β-hydroxy-17α-propinyl-estra-4,9-dien-3-one

TABLE 2

Early Abortive Action in Rats after
Subcutaneous Administration from the 5th to
7th Day of Pregnancy [Administration 0.2 ml/
Animal/Day in Benzoyl Benzoate/Castor Oil) (1 + 4 v/v)

| Substance | Dose (mg/Animal/Day) | Complete Inhibition of Pregnancy* $N^\#/N$ | |
|---|---|---|---|
| Vehicle | | 0/6 | 0 |
| Example 1 | 1 | 4/4 | 100 |
| | 0.3 | 4/4 | 100 |
| | 0.1 | 1/4 | 75 |
| | 0.03 | 0/6 | 0 |
| Example 2 | 1 | 5/5 | 100 |
| Example 3 | 1 | 4/4 | 100 |
| Example 4 | 1 | 2/4 | 50 |
| Example 6 | 1 | 4/4 | 100 |
| | 0.3 | 4/4 | 100 |
| | 0.1 | 0/4 | 0 |
| RU 486** | 3 | 5/5 | 100 |
| | 1 | 1/5 | 20 |
| | 0.3 | 0/5 | 0 |
| ZK 230 211*** | 3 | 4/4 | 100 |
| | 1 | 3/4 | 75 |
| | 0.3 | 0/6 | 0 |

*Empty Uteri
**RU 486: 11β-(4-Dimethylaminophenyl)-17β-hydroxy-17α-propinyl-estra-4,9-dien-3-one
***ZK 230211: 11β-(4-Acetylphenyl)-17β-hydroxy-17α-(1,1,2,2,2-pentafluoroethyl)-estra-4,9-dien-3-one
N: Number of paired females
$N^\#$: Number of nonpregnant females The compounds according to the invention are suitable for postmenopausal substitution therapy and for treatment of gynecological diseases, such as hysteromyomas, as well as for treatment of dysmenorrhoic symptoms.

Subjects of this invention are also pharmaceutical substances (pharmaceutical preparations) for oral, rectal, subcutaneous, intravenous or intramuscular use, which together with commonly used vehicles and optionally diluents contain at least one compound with general formula I as active ingredient.

Pharmaceutical agents according to the invention are produced with commonly used solid or liquid vehicles and/or diluents and the common generally used adjuvants corresponding to the desired type of administration in a suitable dosage and in a way that is known in the art. In a preferred oral dispensing form, preferably tablets, film tablets, coated tablets, capsules, pills, powders, solutions or suspensions are also prepared as a depot form.

In addition, parenteral dosage forms, such as injection solutions or else suppositories, are taken into consideration.

Dosage forms as tablets can be produced, for example, by mixing active ingredient with known adjuvants, such as dextrose, sugar, sorbitol, mannitol, polyvinyl pyrrolidone, explosives, such as corn starch or alginic acid, binders, such as starch or gelatin, lubricants, such as magnesium stearate or talc, and/or agents that can achieve a depot effect, such as carboxypolymethylene, carboxymethyl cellulose, cellulose acetate phthalate or polyvinyl acetate. The tablets can also consist of several layers.

Coated tables analogously can be prepared by coating cores, which are produced analogously to the tablets, with agents that are commonly used in tablet coatings, for example polyvinyl pyrrolidone or shellac, gum arabic, talc, titanium dioxide or sugar. The shell of the coated tablet in this case can also consist of several layers, whereby, for example, the above-mentioned adjuvants are used.

The solutions or suspensions with the active ingredient according to the invention can be mixed for improving the taste with substances, such as saccharine, cyclamate or sugar, and/or with flavoring substances, such as vanilla or orange extract. In addition, they can be mixed with suspension adjuvants, such as sodium carboxymethyl cellulose, or preservatives, such as p-hydroxybenzoic acid.

The capsules can be produced by mixing pharmaceutical substance with vehicles, such as lactose or sorbitol, which then are introduced into the capsules.

Suppositories can preferably be produced by mixing active ingredient with suitable carrier materials, such as neutral fats or polyethylene glycols or derivatives thereof.

The galenical preparation contains the active ingredients in an amount of 1–100 mg, whereby when used in humans, amounts in the range of 1–600 mg per day are required.

This invention is explained, but not limited, by the subsequent examples.

EXAMPLE 1 a) Production of the Starting Compound:
4-[17β-Hydroxy-17α-(1,1,1-trifluoromethyl)-3-oxoestra-4,9-dien-11β-yl]benzaldehyde 1 g of 3,3-dimethoxy-11β-{[4-(1,1-ethylenedioxy)methyl]phenyl}-5α-hydroxy-estr-9-en-17-one is dissolved in 30 ml of absolute THF, mixed with 1.0 g of molecular sieve 3 Å, and stirred for 30 minutes under argon. It is cooled to 0° C., 1.5 ml of trifluoromethyltrimethylsilane is added, it is stirred for 10 more minutes, and then 1 g of tetrabutylammonium fluoride is added. After 10 minutes at 5° C., the reaction solution is decomposed by adding 10 ml of 1N HCl. It is allowed to reach room temperature, in each case 100 ml of water and ethyl acetate are added, the phases are separated, the organic phase is washed neutral, dried on sodium sulfate, the organic phase is filtered off and concentrated by evaporation under vacuum. After acetone is added, 1.05 g of yellow crystals remains. Recrystallization from acetone and treatment with tert-butylmethyl ether yield 480 mg of 4-[17β-hydroxy-17α-(1,1,1-trifluoromethyl)-3-oxoestra-4,9-dien-11β-yl]benzaldehyde. The mother liquor is purified by means of chromatography and yields another 320 mg of aldehyde product.

Melting point: 284–292° C. (acetone)
$\alpha_D$=+221° (CHCl$_3$)
$^1$H-NMR: [300 MHz, CDCl$_3$, TMS]: 0.58 (s, 3H, H-18); 4.51 (d, 1H, J=7.1 Hz, H-11α), 5.81 (s, 1H, H-4), 7.38 (d, 2H, J=8.3 Hz, CH-arom.); 7.81 (d, 2H, J=8.3 Hz), 9.97 (s, 1H, CH=O).

MS (m/e, 70 eV): 444.19061 (M$^+$, 100%), 426.18390 (M$^+$-H$_2$O).

b) Production of the Compound According to the Invention:
4-[17β-Hydroxy-17α-(trifluoromethyl)-3-oxoestra-4,9-dien-11β-yl]benzaldehyde-(1E)-oxime (Compound No. 1):

549 mg of 4-[17β-hydroxy-17α-(trifluoromethyl)-3-oxoestra-4,9-dien-11β-yl]benzaldehyde is dissolved in 5 ml of pyridine, mixed with 83 mg of hydroxylamine hydrochloride and stirred for 1.5 hours at room temperature. Then, the solution is stirred into ice water. The precipitate is suctioned off, washed with water and dried. The crude product is purified by means of chromatography on silica gel (0.05–0.063 mm) with a hexane/ethyl acetate gradient. 493 mg of crude product is obtained, which is recrystallized from tert-butyl methyl ether/n-hexane.

Melting point: 163–167° C. while decomposing (tert-butyl methyl ether/n-hexane)
$\alpha_D$=+244° (CHCl$_3$)
$^1$H-NMR: [300 MHz, CDCl$_3$, TMS]: 0.60 (s, 3H, H-18); 4.44 (d, 1H, J=7.1 Hz, H-11α), 5.80 (s, 1H, H-4), 7.20 (d, 2H, J=8.3 Hz, CH-arom.); 7.50 (d, 2H, J=8.3 Hz); 7.70 (s, 1H, NOH), 8.10 (s, 1H CH=N).

MS (m/e, 70 eV): 459.20001 (M$^+$), 442.199931 (M$^+$-OH, 100%).

EXAMPLE 2 a) Production of the Starting Compound:
4-[17β-Hydroxy-17α-(1,1,2,2,2-pentafluoroethyl)-3-oxoestra-4,9-dien-11β-yl]-benzaldehyde 20 g of 3,3-dimethoxy-11β-{[4-(1,1-ethylenedioxy)methyl]phenyl}-5α-hydroxy-estr-9-en-17-one is suspended in 600 ml of diethyl ether and cooled to −78° C. while being stirred. 48 g of pentafluoroethyl iodide is added, and then 76 ml of a 1.5 ml solution of methyllithium-lithium bromide complex in diethyl ether is slowly added in drops. It is stirred for 2 hours at −78° C. and then poured into 2 l of saturated sodium bicarbonate solution. Then, it is extracted with ethyl acetate, dried and concentrated by evaporation. The residue is taken up in 200 ml of 70% acetic acid and heated for 60 minutes to 60° C. It is allowed to cool and mixed with 400 ml of water, whereby the product precipitates. The precipitate is suctioned off, washed with water and boiled with tert-butyl methyl ether. 4-[17β-Hydroxy-17α-(1,1,2,2,2-pentafluoroethyl)-3-oxoestra-4,9-dien-11β-yl]benzaldehyde is obtained.

Melting point: 220–230° C. (tert-butyl methyl ether)
$^1$H-NMR (CDCl$_3$): 0.58 (s, 3H, H-18), 4.52 (d, 1H, J=7.03 Hz, H-11α), 5.81 (s, 1H, H-4), 7.38 (d, 2H, J=7.81 Hz, CH-arom.); 7.81 (d, 2H, J=8.6 Hz), 9.96 (s, 1H, CH=O).
$^{19}$F-NMR: 77.8 (3F,CF$_3$), 119 (2F,CF$_2$)

b) Production of the Compound According to the Invention:
4-[17β-Hydroxy-17α-(1,1,2,2,2-pentafluoroethyl)-3-oxoestra-4,9-dien-11β-yl]-benzaldehyde-(1E)-oxime (Compound No. 4)

2.5 g of 4-[17β-hydroxy-17α-(1,1,2,2,2-pentafluoroethyl)-3-oxoestra-4,9-dien-11β-yl]-benzaldehyde is dissolved in 32 ml of pyridine and reacted with 450 mg of hydroxylamine-hydrochloride within 4 hours at room temperature. It is poured into ice water, the precipitate is suctioned off, dried and purified by means of chromatography. After recrystallization from acetone, 4-[17β-hydroxy-17α-(1,1,2,2,2-pentafluoroethyl)-3-oxoestra-4,9-dien-11β-yl]benzaldehyde-(1E)-oxime is obtained.

Melting point: 220–230° C.
$^1$H-NMR: 0.59 (s, 3H, H-18); 4.45 (d, 1H, J=6.6 Hz, H-11α), 5.80 (s, 1H, H-4), 7.20 (d, 2H, J=8.2 Hz, CH-arom.); 7.48 (d, 2H, J=8.2 Hz); 8.10 (s, 1H CH=N), 8.24 (s, 1H, NOH), $^{19}$F-NMR: 77.3 (3F,CF$_3$), 119 (2F,CF$_2$)

EXAMPLE 3

4-[17β-Hydroxy-17α-(1,1,2,2,2-pentafluoroethyl)-3-oxoestra-4,9-dien-11β-yl]-benzaldehyd-1-one-(1E)-{O-(ethylamino)carbonyl-oxime (Compound No. 6)

1.4 g of 4-[17β-hydroxy-17α-(1,1,2,2,2-pentafluoroethyl)-3-oxoestra-4,9-dien-11β-yl]-benzaldehyde-(1E)-oxime (compound no. 4) is dissolved in 50 ml of toluene, mixed with 2.26 ml of triethylamine as well as 1.2 ml of ethyl isocyanate and heated to 60° C. The mixture is stirred for 1.5 hours, cooled to 10° C., mixed with 25 ml of aqueous ammonia solution as well as 100 ml of ethyl acetate and stirred for 30 minutes. After the phase separation, the organic phase is washed neutral with water, dried with sodium sulfate and concentrated by evaporation under vacuum. The residue is recrystallized from ethyl acetate. 4-[17β-Hydroxy-17α-(1,1,2,2,2-pentafluoroethyl)-3-oxoestra-4,9-dien-11β-yl]benzaldehyd-1-one-(1E)-{O-(ethylamino)carbonyl-oxime is obtained.

Melting point: 140–146° C. (ethyl acetate)

$^1$H-NMR: 0.59 (s, 3H, H-18), 1.24 (t, 3H J=7.2 Hz, CH$_2$CH$_3$), 4.12 (d, J=6.8 Hz, 1H, H-11), 5.80 (s, 1H, H-4), 6.2 (t, 1H J=5.7 Hz, —NH—), 7.27 and 7.59 (2d; 2H, J=9 Hz, and CH-arom. each), 8.29 (s, 1H, CH=N).

$^{19}$F-NMR (386 MHz): 77.6 (3F,CF$_3$), 119 (2F,CF$_2$)

EXAMPLE 4 a) Production of the Starting Compound:

a1) Stage A:

11β-{[4-(1,1-Ethylenedioxy)methyl]phenyl}-17α-(1,1,2,2,2-pentafluoroethyl)-3,3,17β-trimethoxy-estr-9-en-5α-ol 602 mg of 3,3-dimethoxy-11β-{[4-(1,1-ethylenedioxy)methyl]phenyl}-17α-(1,1,2,2,2-pentafluoroethyl)-estr-9-ene-5α,17β-diol is dissolved while being cooled and under argon cover gas in 5 ml of toluene. 232 mg of potassium-tert-butanolate is added in portions alternately with methyl iodide in toluene over 2 hours. After 3 hours, it is mixed with 20 ml of water, and the phases are separated. The aqueous phase is extracted again with toluene, the combined extracts are washed neutral and dried on sodium sulfate.

After concentration by evaporation, 662 mg of crude product is obtained as a foam, which is used without further purification in stage B.

$^1$H-NMR: [400 MHz, CDCl$_3$, TMS]: 0.56 (s, 3H, H-18); 2.35 (s, 1H, OH), 3.20 and 3.22 (2s; 3H, and 2×OCH$_3$ each), 3.33 (s, 3H, OCH$_3$), 4.08 (m, 4H, ethylene ketal), 4.29 (d, 1H, J=7.2 Hz, H-11α), 4.62 (s, 1H, CH), 5.74 (s, 1H, 5-OH), 7.23 (d, 2H, J=8.0 Hz, CH-arom.); 7.37 (d, 2H, J=8.0 Hz, arom. CH)

a2) Stage B:

4-[17β-Methoxy-17α-(1,1,2,2,2-pentafluoroethyl)-3-oxoestra-4,9-dien-11β-yl]-benzaldehyde 640 mg of 11β-{[4-(1,1-ethylenedioxy)methyl]phenyl}-17α-(1,1,2,2,2-pentafluoroethyl)-3,3,17β-trimethoxy-estr-9-en-5α-ol is dissolved under argon cover gas in 10 ml of acetone, mixed with 300 mg of p-toluenesulfonic acid and stirred for 1 hour at room temperature. The reaction solution is stirred into 500 ml of ice water, whereby a product precipitates in a flocculent manner. It is neutralized with aqueous sodium bicarbonate solution, the precipitate is suctioned off, the filtrate is washed with water and dried. 411 mg of crude product, which is purified with the aid of preparative layer chromatography, is obtained.

Melting point: 160–162° C. (CH$_2$Cl$_2$, tert-butyl methyl ether, n-hexane)

$\alpha_D$=+200° (CHCl$_3$)

$^1$H-NMR: [400 MHz, CDCl$_3$, TMS]: 0.61 (s, 3H, H-18); 3.36 (s, 3H, OCH$_3$), 4.49 (d, 1H, J=6.8 Hz, H-11α), 5.80 (s, 1H, H-4), 7.38 (d, 2H, J=7.6 Hz, CH-arom); 7.81 (d, 2H, J=8.8 Hz), 9.96 (s, 1H, CH=O).

$^{19}$F-NMR (386 MHz): 78.3 (s), 110.5 (d) and 113.7 (d)

b) Production of the Compound According to the Invention:

4-[17β-Methoxy-17α-(1,1,2,2,2-pentafluoroethyl)-3-oxoestra-4,9-dien-11β-yl]-benzaldehyde-(1E)-oxime (Compound No. 13)

This compound is produced according to the instructions of Example 2 from 4-[17β-methoxy-17α-(1,1,2,2,2-pentafluoroethyl)-3-oxoestra-4,9-dien-11-yl]-benzaldehyde with hydroxylamine hydrochloride in pyridine.

Melting point: 122–124° C. (tert-butyl methyl ether)

$\alpha_D$=+188° (CHCl$_3$)

$^1$H-NMR: [400 MHz, CDCl$_3$, TMS]: 0.64 (s, 3H, H-18); 3.36 (s, 3H, OCH$_3$), 4.44 (d, 1H, J=6.4 Hz, H-11α), 5.79 (s, 1H, H-4), 7.21 (d, 2H, J=7.6 Hz, CH-arom.); 7.49 (d, 2H, J=8.4 Hz); 8.02 (s, 1H, NOH), 8.10 (s, 1H CH=N).

EXAMPLE 5

4-[17β-Methoxy-17α-(1,1,2,2,2-pentafluoroethyl)-3-oxoestra-4,9-dien-11β-yl]-benzaldehyd-1-one-(1E)-{O-[(4'-trifluoromethoxy)phenylamino]carbonyl-oxime This compound is produced according to Example 3 from 4-[17β-methoxy-17α-(1,1,2,2,2-pentafluoroethyl)-3-oxoestra-4,9-dien-11β-yl]benzaldehyde-(1E)-oxime with 4-trifluoromethoxymethylphenylisocyanate in toluene.

Colorless foam $\alpha_D$=+149° (chloroform)

$^1$H-NMR (400 MHz, CDCl$_3$, δ in ppm, TMS): 0.64 (s, 3H, H-18), 3.36 (s, 3H, OCH$_3$), 4.48 (d, J=6.8 Hz, 1H, H-11), 5.80 (s, 1H, H-4), 7.21 and 7.54 (2d; 2H, J=8.8 Hz, and CH-arom. each), 7.31 and 7.65 (2d; 2H, J=8.0 Hz, and CH-arom. each), 8.16 (s, 1H, NH), 8.37 (s, 1H, CH=N).

$^{19}$F-NMR (386 MHz): 58.4 (s), 78.3 (s), 110.7 (d) and 113.8 (d)

EXAMPLE 6 a) Production of the Starting Material:

a1) Stage A:

4-[3,3-Dimethoxy-5α,17β-dihydroxy-17α-[(1,1,1-trifluoroethyloxy)methyl]-estr-9-en-11β-yl]benzaldehyde-ethylene ketal 70 ml of DMSO is stirred with 1.54 g of potassium-tert-butanolate at room temperature. 0.8 ml of trifluoroethanol is added in drops, stirred for 10 minutes, and then a solution of 1.36 g of 4-(3,3-dimethoxy-5α-hydroxy-17(S)-spiroepoxy-estr-9-en-11β-yl)-benzaldehyde-ethylene ketal in 30 ml DMSO is added. Under argon cover gas, it is heated to 40° C. After 3 and 5 hours in each case, another 0.8 ml of trifluoroethanol and 1.54 g of potassium-tert-butanolate are added. After 12 hours, it is mixed with aqueous NH$_4$Cl solution and shaken out with toluene. After the usual working-up, 2.8 g of crude product is obtained, which is purified by chromatography on silica gel. This prepared product is used directly in the next stage.

$\alpha_D$=−1° (CHCl$_3$)

MS: m/e 596.29809 M$^+$ (C$_{32}$H$_{43}$F$_3$O$_7$)

a2) Stage B:

4-[17β-Hydroxy-17α-[(1,1,1-trifluoroethyloxy)methyl]-3-oxoestra-4,9-dien-11β-yl]-benzaldehyde 862 mg of 4-[3,3-dimethoxy-5α,17β-dihydroxy-17α-(1,1,1-trifluoroethyloxymethyl)-estr-9-en-11β-yl-benzaldehyde-ethylene ketal is dissolved in 15 ml of acetone, mixed with 1.5 ml of water and 350 mg of p-toluenesulfonic acid and stirred for 1 hour at room temperature. It is diluted with water and extracted with methylene chloride. The organic phase is washed neutral, dried and concentrated by evaporation. 663 mg of 4-[17β-hydroxy-17α-(1,1,1-trifluoroethyloxymethyl)-3-oxoestra-4,9-dien-11β-yl]benzaldehyde is obtained as a foam. The crude product is purified by preparative layer chromatography.

Melting point: 100–103° C. (ether)

$\alpha_D$=+169° (CHCl$_3$)

$^1$H-NMR: [400 MHz, CDCl$_3$, TMS]: 0.53 (s, 3H, H-18); 3.45 and 3.91 (2m, 2×CH$_2$); 4.45 (d, 1H, J=7.2 Hz, H-11α), 5.81 (s, 1H, H-4), 7.37 (d, 2H, J=8.1 Hz, CH-arom.); 7.81 (d, 2H, J=8.1 Hz), 9.98 (s, 1H, CH=O).

b) Production of the Compound According to the Invention: 4-[17β-Hydroxy-17α-(1,1,1-trifluoroethyloxymethyl)-3-oxoestra-4,9-dien-11β-yl]-benzaldehyde-(1E)-oxime (Compound No. 22)

For the production of the title compound, 340 mg of 4-(17β-hydroxy-17α-(1,1,1-trifluoroethyloxymethyl)-3-oxoestra-4,9-dien-11β-yl]benzaldehyde according to Example 2 is reacted. 326 mg of crude product is obtained. The crude product is purified by preparative layer chromatography on silica gel PF$_{254}$ nm.

Melting point: 132–136° C. (ether)

$\alpha_D$+182°

$^1$H-NMR (400 MHz, CDCl$_3$, δ in ppm, TMS): 0.55 (s, 3H, H-18), 3.45 and 3.89 (m; 2H and CH$_2$ each), 4.39 (d, J=6.8 Hz, 1H, H-11), 5.80 (s, 1H, H-4), 7.20 and 7.49 (2d; 2H, J=8.4 Hz, and CH-arom. each), 7.60 (s, 1H, OH), 8.11 (s, 1H, CH=N).

$^{19}$F-NMR (386 MHz): 58.4 (s), 78.3 (s), 110.7 (d) and 113.8 (d)

EXAMPLE 7 a) Production of the Starting Compound: 4-[17β-Hydroxy-17α-(1,1,2,2,3,3,3-heptafluoropropyl)-3-oxoestra-4,9-dien-11β-yl]-benzaldehyde 965 mg of 3,3-dimethoxy-11β-{[4-(1,1-ethylenedioxy)methyl]phenyl}-5α-hydroxy-estr-9-en-17-one is dissolved in 35 ml of absolute THF, mixed with 1.0 g of molecular sieve 3 Å and stirred for 30 minutes under argon. It is cooled to 0° C., 0.5 ml of 1,1,2,2,3,3,3-heptafluoropropyltrimethylsilane is added in drops, stirred for 10 more minutes, and then 55 mg of tetrabutylammonium fluoride is added. After 10 minutes at 5° C., the reaction solution is decomposed by adding 10 ml of 1N HCl. It is allowed to reach room temperature, stirred for 2 more hours, cooled again to 0° C., and another 0.5 ml of 1,1,2,2,3,3,3-heptafluoropropyltrimethylsilane is added. After 15 minutes, the solution is hydrolyzed by adding 15 ml of 1N HCl. After another 30 minutes, 100 ml of saturated ammonium chloride solution is added, and the solution is extracted with ethyl acetate. The organic phase is washed neutral, dried on sodium sulfate, the organic phase is filtered off and concentrated by evaporation under vacuum. The brown crude product (924 mg) is purified by means of chromatography on silica gel with ethyl acetate/n-hexane 1:2. Recrystallization from acetone/n-hexane yields 485 mg of 4-[17β-hydroxy-17α-(1,1,2,2,3,3,3-heptafluoropropyl)-3-oxoestra-4,9-dien-11β-yl]-benzaldehyde.

b) Production of the Compound According to the Invention: 4-[17β-Hydroxy-17α-(1,1,2,2,3,3,3-heptafluoropropyl)-3-oxoestra-4,9-dien-11β-yl]-benzaldehyde-(1E)-oxime (Compound No. 10)

The title compound is produced according to Example 2 from 4-[17β-hydroxy-17α-(1,1,2,2,3,3,3-heptafluoropropyl)-3-oxoestra-4,9-dien-11β-yl] benzaldehyde by reaction with hydroxylamine hydrochloride in pyridine.

Melting point 170–175° C.

$^1$H-NMR: 0.59 (s, 3H, H-18); 4.45 (d, 1H, J=6.6 Hz, H-11α), 5.80 (s, 1H, H-4), 7.20 (d, 2H, J=8.2 Hz, CH-arom.); 7.48 (d, 2H, J=8.2 Hz); 8.10 (s, 1H CH=N), 8.24 (s, 1H, NOH)

As one skilled in the art can easily discern, any changes and modifications to the preferred embodiments of the invention shown here are included in the scope of protection of the attached claims. This also means that any combinations of features of this invention are included in the disclosure content.

What is claimed is:

1. 17α-Fluoroalkyl-11β-benzaldoxime steroids with general formula I

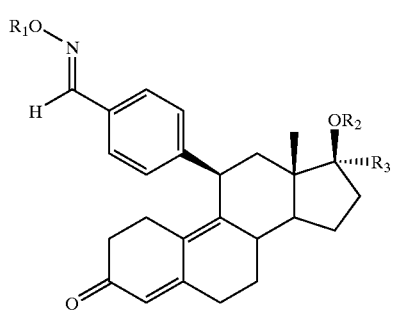

in which

R$_1$ stands for hydrogen, C$_1$- to C$_6$-alkyl, COR$_4$, COOR$_4$, COSR$_4$ or CONHR$_5$, in which R$_4$ is C$_1$- to C$_6$-alkyl or unsubstituted or substituted aryl and in which R$_5$ is hydrogen, C$_1$- to C$_6$-alkyl or unsubstituted or substituted aryl, R$_2$ stands for hydrogen, C$_1$- to C$_6$-alkyl or C$_1$- to C$_6$-acyl, and R$_3$ stands for a C$_n$F$_{2n+1}$ group, in which n=1, 2 or 3, or for a CH$_2$O(CH$_2$)$_m$C$_n$F$_{2n+1}$ group, in which m=0 or 1 and n=1, 2 or 3, as well as their pharmaceutically compatible salts.

2. 17α-Fluoroalkyl-11β-benzaldoxime steroids according to claim 1, characterized in that R$_1$ stands for hydrogen, methyl, formyl, acetyl, propionyl, benzoyl, methoxycarbonyl, ethoxycarbonyl, methylthiocarbonyl, ethylthiocarbonyl, ethylaminocarbonyl or unsubstituted or substituted phenylaminocarbonyl.

3. 17α-Fluoroalkyl-11β-benzaldoxime steroids according to claim 2, wherein the substituted phenylaminocarbonyl radical is substituted with a C$_1$- to C$_6$-perfluoroalkyl radical.

4. 17α-Fluoroalkyl-11β-benzaldoxime steroids according to claim 1, wherein R$_2$ stands for hydrogen, methyl or acetyl.

5. 17α-Fluoroalkyl-11β-benzaldoxime steroids according to claim 1, wherein R$_3$ stands for 1,1,1-trifluoromethyl, 1,1,2,2,2-pentafluoroethyl, 1,1,2,2,3,3,3-heptafluoropropyl or 1,1,1-trifluoroethyloxymethyl.

6. 17α-Fluoroalkyl-11β-benzaldoxime steroids according to claim 1, namely 1) 4-[17α-Hydroxy-17α-(1,1,1-trifluoromethyl)-3-oxoestra-4,9-dien-11β-yl]benzaldehyde-1(E)-oxime 2) 4-[17β-Hydroxy-17α-(1,1,1-trifluoromethyl)-3-oxoestra-4,9-dien-11β-yl]benzaldehyde-1(Z)-oxime 3) 4-[17β-Hydroxy-17α-(1,1,1-trifluoromethyl)-3-oxoestra-4,9-dien-11β-yl]benzaldehyde-1(E)-[O-(ethylamino)carbonyl]oxime 4) 4-[17β-Hydroxy-17α-(1,1,2,2,2-pentafluoroethyl)-3-oxoestra-4,9-dien-11β-yl]benzaldehyde-1(E)-oxime
5) 4-[17β-Hydroxy-17α-(1,1,2,2,2-pentafluoroethyl)-3-oxoestra-4,9-dien-11β-yl]benzaldehyde-1(E)-O-acetyloxime
6) 4-[17β-Hydroxy-17α-(1,1,2,2,2-pentafluoroethyl)-3-oxoestra-4,9-dien-11β-yl]benzaldehyde-1(E)-[O-(ethylamino)carbonyl]oxime
7) 4-[17β-Hydroxy-17α-(1,1,2,2,2-pentafluoroethyl)-3-oxoestra-4,9-dien-11β-yl]benzaldehyde-1(E)-[O-(ethylthio)carbonyl]oxime
8) 4-[17α-Hydroxy-17α-(1,1,2,2,2-pentafluoroethyl)-3-oxoestra-4,9-dien-11β-yl]benzaldehyde-1(E)-[O-(ethoxy)carbonyl]oxime
9) 4-[17β-Hydroxy-17α-(1,1,2,2,2-pentafluoroethyl)-3-oxoestra-4,9-dien-11β-yl]benzaldehyde-1(E)-[O-(methoxy)carbonyl]oxime
10) 4-[17β-Hydroxy-17α-(1,1,2,2,3,3,3-heptafluoropropyl)-3-oxoestra-4,9-dien-11β-yl]benzaldehyde-1(E)-oxime
11) 4-[17β-Methoxy-17α-(1,1,1-trifluoromethyl)-3-oxoestra-4,9-dien-11β-yl]benzaldehyde-1(E)-oxime
12) 4-[17β-Methoxy-17α-(1,1,1-trifluoromethyl)-3-oxoestra-4,9-dien-11β-yl]benzaldehyde-1(E)-[O-(ethylamino)carbonyl]oxime
13) 4-[17β-Methoxy-17α-(1,1,2,2,2-pentafluoroethyl)-3-oxoestra-4,9-dien-11β-yl]benzaldehyde-1(E)-oxime
14) 4-[17β-Methoxy-17α-(1,1,2,2,2-pentafluoroethyl)-3-oxoestra-4,9-dien-11β-yl]benzaldehyde-1(E)-O-acetyloxime
15) 4-[17β-Methoxy-17α-(1,1,2,2,2-pentafluoroethyl)-3-oxoestra-4,9-dien-11β-yl]benzaldehyde-1(E)-[O-(ethylamino)carbonyl]oxime
16) 4-[17β-Methoxy-17α-(1,1,2,2,2-pentafluoroethyl)-3-oxoestra-4,9-dien-11β-yl]benzaldehyde-1(E)-{O-[(4'-trifluoromethyloxy)phenyl-amino]carbonyl}oxime
17) 4-[17β-Methoxy-17α-(1,1,2,2,2-pentafluoroethyl)-3-oxoestra-4,9-dien-11β-yl]benzaldehyde-1(E)-[O-(ethoxy)carbonyl]oxime
18) 4-[17-Methoxy-17α-(1,1,2,2,2-pentafluoroethyl)-3-oxoestra-4,9-dien-11β-yl]benzaldehyde-1(E)-[O-(methoxy)carbonyl]oxime
19) 4-[17β-Methoxy-17α-(1,1,2,2,2-pentafluoroethyl)-3-oxoestra-4,9-dien-11β-yl]benzaldehyde-1(E)-[O-(ethylthio)carbonyl]oxime
20) 4-[17β-Acetoxy-17α-(1,1,2,2,2-pentafluoroethyl)-3-oxoestra-4,9-dien-11β-yl]benzaldehyde-1(E)-[O-(ethylamino)carbonyl]oxime
21) 4-[17β-Acetoxy-17α-(1,1,2,2,2-pentafluoroethyl)-3-oxoestra-4,9-dien-11β-yl]benzaldehyde-1(E)-oxime
22) 4-[17β-Hydroxy-17α-[(1,1,1-trifluoroethyloxy)methyl]-3-oxoestra-4,9-dien-11β-yl]benzaldehyde-1(E)-oxime.

7. Process for the production of 17α-fluoroalkylated 11β-benzaldoxime steroids with general formula I

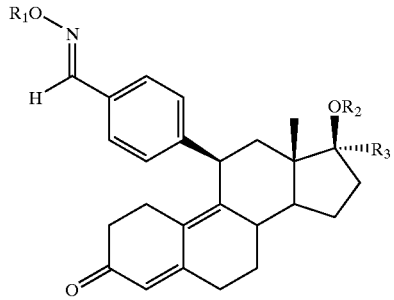

in which radicals $R_1$, $R_2$ and $R_3$ have the meanings that are indicated in claim 1, wherein an 11β-benzaldehyde with general formula II

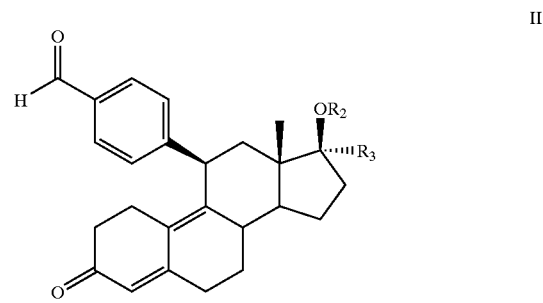

is reacted with a salt of a hydroxylamine in a basic solution, so that a 17α-fluoroalkyl-11β-benzaldoxime steroid is produced, in which $R_1$ is hydrogen, and this compound optionally is esterified, etherified or converted into a corresponding carbamate, carboxylic acid derivative or thiocarboxylic acid derivative.

8. Process according to claim 7, wherein the salt of the hydroxylamine is a hydrochloride or hydrosulfate.

9. Process according to claim 7, wherein the basic solvent is pyridine.

10. Pharmaceutical preparation that contains at least one 17α-fluoroalkyl-11β-benzaldoxime steroid with the general formula I according to claim 1 as well as at least one pharmaceutically compatible vehicle.

* * * * *